United States Patent [19]
Hubner et al.

[11] Patent Number: 5,618,957
[45]* Date of Patent: Apr. 8, 1997

[54] METHOD OF PRODUCING SALCOMINE

[75] Inventors: Frank Hubner, Ober-Ramstadt; Ulrich Gora; Klaus Huthmacher, both of Gelnhausen; Karlheinz Drauz, Freigericht, all of Germany

[73] Assignee: Degussa AG, Frankfurt, Germany

[21] Appl. No.: 535,634

[22] Filed: Sep. 28, 1995

[30] Foreign Application Priority Data

Sep. 30, 1994 [DE] Germany .......................... 44 35 158.5

[51] Int. Cl.$^6$ .................................................. C07F 15/06
[52] U.S. Cl. .............................................. 556/32; 556/150
[58] Field of Search ........................................ 556/32, 150

[56] References Cited

U.S. PATENT DOCUMENTS 2,508,490  5/1950  Calvin et al. ........................ 260/439

FOREIGN PATENT DOCUMENTS 3302498  7/1984  Germany .

OTHER PUBLICATIONS

Bailes et al., "The Oxygen–carrying Synthetic Chelate Compounds". VII. Preparation[1], *Journal of the American Chemical Society*, vol. 69, 1947, pp. 1886–1893.

Aymes et al., "Synthèse de complexes du cobalt (II) avec des bases de Schiff: complexes porteurs d'oxygène", *Bulletin de la Societe Chimique de France*, No. 315, 1976, pp. 1717–1721.

Aymes et al., "Molecular Oxygen Uptake by a Solid Co(II) Complex", *Journal of Chemical Education*, vol. 66, No. 10, Oct. 1989, pp. 854–856.

*Primary Examiner*—Porfirio Nazario-Gonzalez
*Attorney, Agent, or Firm*—Cuhman Darby & Cushman IP Group of Pillsbury Madison & Sutro LLP

[57] ABSTRACT

A method of producing salcomine by reacting ethylene diamine with salicylaldehyde and a cobalt salt in a liquid reaction medium containing solvent.

15 Claims, No Drawings

METHOD OF PRODUCING SALCOMINE

BACKGROUND OF THE INVENTION

1. Field of the Invention

The invention relates to a method of producing salcomine in which ethylene diamine is reacted with approximately twice the molar amount of salicylaldehyde, relative to ethylene diamine, and with a cobalt salt using a solvent in a liquid reaction medium at temperatures of 60°–150° C.

2. Description of the Related Art

Salcomine, that is, N,N-bis-salicylidene ethylene diimine cobalt (II) of the formula

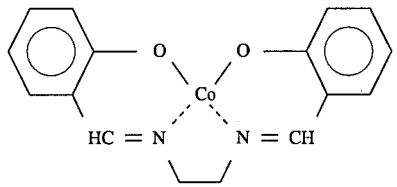

is a very suitable catalyst for the oxidation of alkylated phenols to the corresponding alkylated p-benzoquinones, especially for the oxidation of 2,3,6-trimethylphenol to 2,3,5-trimethyl-p-benzoquinone, which can be readily converted by hydrogenation into 2,3,5-trimethylhydroquinone. For its part, trimethylhydroquinone is very interesting as an intermediate [i. product] for vitamin E.

In known methods for the production of salcomine the reaction of ethylene diamine and salicylaldehyde with a cobalt (II) salt takes place e.g. in aqueous or aqueous-organic solution.

The presence of a buffer (e.g. aqueous acetic acid sodium acetate solution or an alkanol-pyridine mixture) is also recommended for a better dissolving of the Schiff base of salicylaldehyde and the diamine. The precipitating salcomine must finally be filtered off, washed several times and dried.

In particular, an expensive workup requiring filtration, several washings and drying is disadvantageous in this method and in other known methods which are collated in D. Aymes, M. R. Paris, Bull. Soc. Chim. Fr. 1976, 1717–21 and D. Aymes, M. R. Paris, J. Chem. Educ., 66 (1989), 854–56.

In addition, the salcomine obtained is not always of a uniform quality as regards its oxidation action.

The improvements suggested by Aymes et al. in the cited literature of using benzene, chloroform or methylene chloride and the cobalt acetylacetonate soluble therein as solvent in the production of salcomine have the disadvantages of low yields of salcomine and the use of expensive cobalt compounds and solvents which are somewhat hazardous to health.

DE 33 02 498 suggests a method of producing salcomine by reacting 2 moles salicylaldehyde with 1 mole ethylene diamine and a cobalt salt in a liquid reaction medium in which the salicylaldehyde is reacted with the ethylene diamine in a linear or cyclic carboxylic acid amide substituted on the nitrogen as solvent and the reaction mixture obtained is reacted at temperatures of 60° to 150° C. with cobalt carbonate or cobalt hydroxide carbonate 2 $CoCO_3 \cdot 3$ $Co(OH)_2$.

In particular, dimethylformamide or N-methylpyrrolidone are examples of solvents according to DE 33 02 498. Although yields of salcomine of up to 99% are reported in the patent under discussion, these high yields were not able to be verified. Contrary to the data in the patent, the yields in reference tests were only approximately 60% for cobalt hydroxy carbonate (see below Reference Example 1 which is approximately equal to example 3 in DE 33 02 498) or approximately 90% when using cobalt carbonate (example 1 in DE 33 02 498). In addition, in the method according to DE 33 02 498, the use of solvents injurious to health appears hazardous.

Methods of producing chiral catalysts similar to salcomine are known from WO 93/03838. However, exclusively trivalent metal complexes are disclosed there.

DE-A-42 38 076 also describes a compound similar to salcomine. However, the solubility behavior of $Co(5-NO_2$-saltmen) is distinctly different from that of salcomine.

SUMMARY OF THE INVENTION

In view of the state of the art discussed here, it is an object of the invention to provide a further method of producing salcomine which eliminates to the extent possible the use of solvents which are injurious or hazardous to the health and at the same time makes possible the highest possible yield of salcomine, preferably equal or superior to that known from the methods according to the state of the art.

These problems and others which are not detailed are solved by a method of the initially mentioned type with the features of the characterizing part of claim 1.

Advantageous variants of the method of the invention are detailed in the claims depending from claim 1.

The fact that one or several aliphatic and/or cycloaliphatic alcohols R—OH, in which R stands for a linear, branched or cyclic $C_3$–$C_{12}$ alkyl group, and/or one or several aromatic hydrocarbons with 6–15 carbon atoms are used as solvent, and cobalt carbonate, basic cobalt carbonate ($CoCO_3 \cdot Co(OH)_2$) and/or cobalt acetate are used as cobalt salt results in considerable advantages in the production of salcomine in accordance with the invention over the state of the art. This includes, among others:

A) Use of the poisonous solvent dimethylformamide is not necessary.

B) The yields of salcomine are approximately 90–99% versus approximately 60% to 90% according to the state of the art (see Reference Examples 1 and 1a, set forth below).

C) The solvent-moist salcomine can be used without further drying for the oxidation of trimethylphenol.

D) The yield of trimethyl-p-benzoquinone is usually above 90%, regardless of whether a start was made from dry or moist catalysts.

E) The reaction water can readily be spun out azeotropically.

F) The salcomine crystallizes out of the mixture in analytical reagent quality.

G) The salcomine produced is stable in storage.

The simple production of salcomine in accordance with the invention, using cobalt salts (such as cobalt carbonate, basic cobalt carbonate or cobalt acetate) which are essentially insoluble in the solvents used, is very surprising, since the prior art teaches that the cobalt salt must be soluble in the solvent used for the reaction; or if cobalt carbonate or basic cobalt carbonate is used, that the solvent must be dimethylformamide or a corresponding linear or cyclic carboxylic acid amide which is disubstituted on the nitrogen.

In contrast to this, the invention has demonstrated, in a manner which could not have been readily foreseen, that the reaction of salicylaldehyde with ethylene diamine and one or several cobalt salts from the group cobalt carbonate, basic cobalt carbonate and cobalt acetate produces excellent results, even when using organic solvents other than DMF or N-methylpyrrolidone, with respect to the yield of salcomine and its quality as oxidation catalyst.

The solvents to be used in accordance with the invention basically include the aliphatic and cycloaliphatic alcohols with 3 to 12 carbon atoms as well as aromatic hydrocarbons with 6 to 15 carbon atoms well-known to experts in the art.

Preferred aromatic solvents to be used in accordance with the invention are toluene, xylenes or other aromatics of formulas I–III substituted with alkyl groups

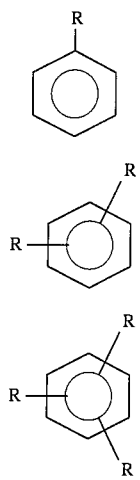

in which R signifies alkyl groups with up to 6 C atoms; however, in a multiple substitution the number of C atoms of all groups is limited to 9 together.

Aromatic hydrocarbons with 6 to 15 C atoms in accordance with the invention are, among others, toluene, cumene, xylene and mesitylene.

Aliphatic and cycloaliphatic alcohols as solvents can be compounds of the formulas IV and V

in which R can be n-alkyl of 3–12 carbon atoms or branched alkyl groups of 3–12 carbon atoms.

This includes, among others, n-propanol, isopropanol, n-butanol, sec.-butanol, tert.-butanol, n-pentanol, isoamyl alcohol, n-hexanol.

In cycloaliphatic alcohols of formula V, n can be a number from 0–9. Exemplary cycloaliphatic alcohols comprise, among others, cyclobutanol, cyclopentanol, cyclohexanol, cycloheptanol and cyclooctanol.

The above-named solvents are used either alone or in a combination of two or more.

Solvents which are especially preferred for the invention are n-butanol or toluene because especially high yields of salcomine are obtained in them and they are relatively non-hazardous and quite economical.

Cobalt carbonate and/or basic cobalt carbonate are to be cited in particular among the salts to be used for the invention. Surprisingly, very high yields were obtained even when using cobalt acetate Co(OAc)$_2$.4 H$_2$O in n-butanol. In particular, a salcomine produced in this manner exhibited an excellent conversion of trimethylphenol to trimethyl-p-benzoquinone in the oxidation reaction.

The finding is again in clear contrast to the state of the art, in which the opinion was advanced that the reaction speeds for the trimethylphenol oxidation with solvent-moist salcomine in the case of salcomines produced from Co(OAc)$_2$ were approximately 10 to 15% lower and that only the salcomine produced from CoCo$_3$ or from cobalt hydroxide carbonate exhibited an unchanged good conversion.

In a preferred variant of the method of the invention, the reaction of salicylaldehyde, ethylene diamine and cobalt salt is carried out while "spinning out" [See point E) above.] the water produced during the reaction, the acetic acid which may be produced during the reaction, and the water contained in the cobalt salt used. It is most advantageous if the "spinning out" (removal) of the water and acetic acid from the reaction mixture takes place azeotropically.

The production of salcomine in accordance with the invention can be made especially advantageous by carrying out the conversion under an atmosphere of inert gas, that is, e.g. under nitrogen or argon.

DETAILED DESCRIPTION OF THE PREFERRED EMBODIMENTS

In order to carry out the method of the invention for producing salcomine, for example, 2 moles (1.5–2.5 moles) salicylaldehyde and 1 mole ethylene diamine are dissolved in the aromatic hydrocarbon or the aliphatic alcohol under nitrogen at approximately 60° C. and after the addition of 1 mole cobalt carbonate or basic cobalt carbonate heated approximately 1 h (0.5–2 h) at boiling temperature. After the separation of approximately 1 mole water the reaction is complete and the salcomine crystallizes out quantitatively.

The invention is explained in detail below using exemplary embodiments.

REFERENCE EXAMPLE 1

The production of salcomine according to the instruction of German patent 33 02 498 (example 3)

244 g (2 moles) salicylaldehyde were dissolved in 700 ml DMF and compounded within 30 min with 60 g (1 mole ethylene diamine. The temperature rose to 60° C. thereby and a yellow, crystalline solid precipitated out. The mixture was subsequently heated to 120° C. and compounded in portions within 30 min with 125 g (1 mole cobalt) CoCO$_3$.Co(OH)$_2$ (cobalt content>47%). After one hour of subsequent reaction at 120° C. under a slight development of gas the mixture was cooled off to room temperature (RT) and the crystalline precipitation filtered off. The yield of dried salcomine was 204 g, corresponding to 63% of theoretical.
CH analysis: Calc. C 59.09 H 4.34 N 8.61
Obs. C 52.20 H 3.82 N 7.50

REFERENCE EXAMPLE 1a

The same procedure was followed as in Reference Example 1, but using the corresponding amount of cobalt carbonate. The yield was approximately 90 of theoretical.

EXAMPLE 2

12.2 g (0.1 mole) salicylaldehyde were dissolved under nitrogen in 125 ml n-butanol, and 3.0 g (0.05 mole) ethylene diamine added dropwise within 15 min at 50° C. The mixture was then agitated an additional 30 min at 60° C. A yellow suspension with crystalline solid was obtained. After the mixture had cooled off to RT, 6.25 g (0.05 mole) basic cobalt carbonate or 6.4 g (0.05 mole) cobalt carbonate (>46% cobalt) were added and the mixture heated to a boil under the continued introduction of nitrogen for 1.5 h.

Approximately 40 ml n-butanol and 2 ml water were distilled off thereby. After cooling off to RT the crystalline precipitation was removed by suction. Yield: 16.1 g dried salcomine corresponding to 99% of theoretical.
CH analysis: Calc. C 59.09 H 4.43 N 8.61
Obs. C 59.10 H 4.41 N 8.70

EXAMPLE 3

The same procedure was used as in Example 2 but instead of n-butanol as solvent 125 ml toluene were used. 14.5 g dried salcomine corresponding to 89% of theoretical were obtained.
CH analysis: Calc. C 59.09 H 4.34 N 8.62
Obs. C 58.27 H 4.28 N 8.45

EXAMPLE 4

The same procedure was used as in Example 2; however, the reaction was with 12.5 g (0.05 mole) cobalt acetate $Co(OAc)_2.4\ H_2O$ instead of basic cobalt carbonate and approximately 2.5 ml water were separated. 16.1 g (99% of theoretical) dried salcomine were obtained.
Calc. C 59.09 H 4.34 N 8.61
Obs. C 57.65 H 4.35 N 8.24

EXAMPLE 5

The same procedure was used as in Example 1; however, the entire operation was carried out under nitrogen. 13.7 g (84% of theoretical) dried salcomine were obtained.
Calc. C 59.09 H 4.34 N 8.61
Obs. C 58.94 H 4.38 N 8.72

REFERENCE EXAMPLE 6 AND EXAMPLES 7–10

Oxidation of 2,3,6-trimethylphenol (TMP) to 2,3,5-trimethyl-p-benzoquinone (TMC)

The salcomines produced in Examples 1–5 were investigated in the oxidation reaction of TMP to TMC. For this, 20 g TMP were dissolved in 59 g (62 ml) DMF and compounded with 0.6 g salcomine (calculated for dry salcomine) of Examples 1–5 in each instance. An oxidation was then carried out with oxygen for 4 h at first at 30° C. and then 2 hours further at 42° C. The trimethyl-p-benzoquinone (TMC) content in the solution was determined by HPLC.

TABLE I

| Example/Reference-example | Salcomine from Example | Cobalt Salt | Solvent for Production of Salcomine | TMC yield (% of theoretical) Salcomine moist | TMC yield (% of theoretical) Salcomine dried |
|---|---|---|---|---|---|
| 6 | 1 (cf. state of the art) | $CoCO_3 \cdot Co(OH)_2$ | DMF | 90.6 | 90.8 |
| 7 | 2 | $CoCO_3$ and $CoCO_3 \cdot Co(OH)_2$ | n-Butanol | 91.8 90.6 | 92.4 90.8 |
| 8 | 3 | $CoCO_3 \cdot Co(OH)_2$ | Toluol | 91.9 | 91.9 |
| 9 | 4 | $Co(OAc)_2 \cdot 4H_2O$ | n-Butanol | 91.8 | 92.2 |
| 10 | 5 | $CoCO_3 \cdot Co(OH)_2$ | DMF | 91.6 | 91.9 |

While the invention has been described in what is presently considered to be the most practical and preferred embodiments, it is to be understood that it is not to be limited by the examples given, but is intended to cover further advantages and embodiments within the scope of the following claims. References cited above are hereby incorporated herein by reference.

What is claimed is:

1. A method of producing salcomine comprising reacting ethylene diamine with an approximately twice molar amount of salicylaldehyde and a cobalt salt in a liquid reaction medium containing solvent at a temperature between about 60° C. and 150° C.; wherein one or several aliphatic and/or cycloaliphatic alcohols R—OH, R representing a linear, branched or cyclic $C_3$–$C_{12}$ alkyl group, and/or one or several aromatic hydrocarbons with 6–15 carbon atoms are used as solvent; and cobalt carbonate, basic cobalt carbonate ($CoCO_3.Co(OH)_2$) and/or cobalt acetate are used as cobalt salt.

2. The method according to claim 1, in which n-butanol is used as solvent.

3. The method according to claim 1, in which cobalt carbonate and/or basic cobalt carbonate is used as cobalt salt.

4. The method according to claim 2, in which cobalt carbonate and/or basic cobalt carbonate is used as cobalt salt.

5. The method according to claim 1, wherein toluene is used as solvent.

6. The method according to claim 3, wherein toluene is used as solvent.

7. The method according to claim 1, additionally comprising spinning out water and/or acetic acid produced during the reaction and spinning out water contained in the cobalt salt.

8. The method according to claim 4, additionally comprising spinning out water and/or acetic acid produced during the reaction and spinning out water contained in the cobalt salt.

9. The method according to claim 6, additionally comprising spinning out water and/or acetic acid produced during the reaction and spinning out water contained in the cobalt salt.

10. The method according to claim 1 wherein the reaction is carried out under a protective gas.

11. The method according to claim 8 wherein the reaction is carried out under a protective gas.

12. The method according to claim 9 wherein the reaction is carried out under a protective gas.

13. The method of claim 10 wherein the protective gas is nitrogen.

14. The method of claim 11 wherein the protective gas is nitrogen.

15. The method of claim 12 wherein the protective gas is nitrogen.

* * * * *